Feb. 26, 1957 C. MALLERIN Plant Pat. 1,573
ROSE PLANT
Filed May 16, 1956
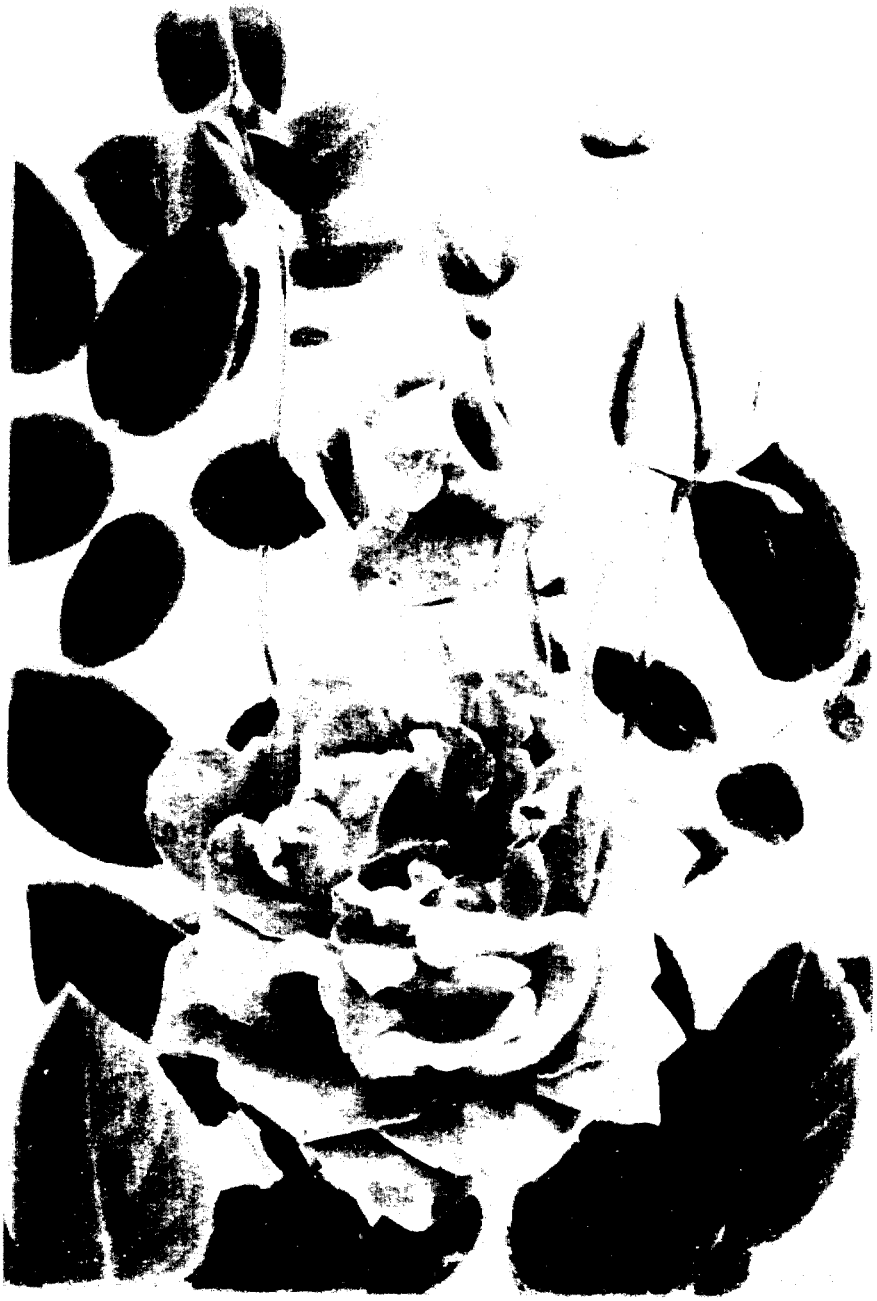
Inventor.
Charles Mallerin
By: Robb & Robb
Attorneys.

United States Patent Office

Plant Pat. 1,573
Patented Feb. 26, 1957

1,573

ROSE PLANT

Charles Mallerin, Varces, Allieres et Risset, France, assignor to The Conard-Pyle Company, West Grove, Pa., a corporation of Pennsylvania Application May 16, 1956, Serial No. 585,373

1 Claim. (Cl. 47—61)

The present invention relates to a new and distinct variety of rose plant of the remontant large-flowered climber class, which was originated by me by crossing two of my previously developed, unnamed and unpatented seedlings.

The primary objective of this breeding was to produce a new climbing rose having remontant characteristics combined with large and well-formed red flowers. In attempting to achieve this objective, I utilized as the female parent a remontant climber bearing semi-double red flowers, shaded with orange, this parent having been derived from a cross of "Holstein" (U. S. Plant Patent No. 395) with the variety named "Record" (unpatented). The male parent which I used was a hybrid tea rose bearing large and well-shaped orange-red flowers and derived from the same cross as that which produced the female parent, namely, "Holstein" × "Record." From the offspring of the new cross aforesaid, I selected the one which best exemplified the objective features and which constitutes the new variety to which this patent application is directed.

My new variety is definitely distinguished from its parents, as well as from all other varieties of which I am aware, as evidenced by the following outstanding features:

(1) A vigorous habit of growth;
(2) Good hardiness;
(3) Abundant and attractive foliage;
(4) Very good remontance;
(5) A habit of producing a terminal bloom on each new shoot;
(6) Very good form and size of the blooms;
(7) A strong and appealing fragrance of the blooms; and
(8) The distinctive iridescent Spirea Red general color tonality of the blooms which clears to iridescent Cardinal Red in cool weather.

Asexual reproduction of my new variety by budding, as performed by me in France, and as performed on my behalf at West Grove, Pennsylvania, U. S. A., shows that the foregoing characteristics come true to form and are established and transmitted through succeeding propagations.

The accompanying drawing shows typical illustrations of the vegetative growth and flowers of my new variety in different stages of development and as depicted in color as nearly true as it is possible to make the same in a color illustration of this character.

The following is a detailed description of my new variety, with color terminology in accordance with the "Horticultural Color Chart of the British Color Council," except where general color terms of ordinary dictionary significance are obvious:

Type: Hardy; climbing; outdoor; seedling; for garden decoration.
Class: Climber.
Breeding: Seedling.
*Seed parent.*—An unnamed remontant climber bearing semi-double red flowers, shaded with orange, and derived from a cross of "Holstein" × "Record."
*Pollen parent.*—An unnamed hybrid tea seedling bearing large and well-shaped orange-red flowers and derived from a cross of "Holstein" × "Record."
Propagation: Holds its distinguishing characteristics through succeeding propagations by budding.

*Flower*

Locality where grown and observed: West Grove, Pennsylvania, U. S. A.
Flowers borne: Usually singly, but sometimes from two to several per stem; on stems of medium length and normal strength.
Quantity of bloom: Free, outdoors.
Continuity: Continuous.
Fragrance: Strong. Nature—tea.
Bud:
*Peduncle.*—Medium length; medium caliper; erect; rough; with medium number of hairs of Garnet Brown, Plate 00918/3. Color—Garnet Brown, Plate 00918/3, overlying Lettuce Green, Plate 861/1.
*Before calyx breaks.*—Size—medium large, but considered large for a climber. Form—short; ovoid; with a conspicuous neck; with slender, bristle-like, foliaceous parts extending beyond the tip of the bud equal to ¼ or more of its length.
*As calyx breaks.*—Color—Currant Red, Plate 821, blotched with Oxblood Red, Plate 00823.
*As first petal opens.*—Size—medium. Form—ovoid. Color: outside—Spirea Red, Plate 025; inside—Iridescent Rose Red, Plate 724.
*Opening.*—Opens up well.
Bloom:
*Size (when fully open).*—Medium large; from 3½ inches to 3¾ inches.
*Petalage.*—Double; from 30 to 35 petals; arranged regularly.
*Form.*—Full and high-centered at first, but becoming cupped; petals being at first loosely rolled outward, and remaining loosely rolled outward at maturity.
Petals: Medium thickness; leathery; with inside velvety and outside satiny.
*Shape.*—Outer petals—round; generally with no notches. Intermediate petals—round; sometimes with one notch, but sometimes with no notches. Inner petals—obovate; generally with no notches.

This description of a newly-opened flower was made from a rose grown outdoors in the early part of September, at West Grove, Pennsylvania, U. S. A.:

*Color.*—Outer petal: outside surface—Spirea Red, Plate 025/1, shading into Cherry, Plate 722/3 towards base of petal, with point of attachment Sulphur Yellow, Plate 1/2; inside surface—Iridescent Rose Red, Plate 724, with point of attachment Aureolin, Plate 3/1. Intermediate petal: outside surface—Rose Bengal, Plate 25/1, shading to Cherry, Plate 722/3, with point of attachment Sulphur Yellow, Plate 1/2; inside surface—Iridescent Rose Red, Plate 724, with point of attachment Aureolin, Plate 3/1. Inner petal: outside surface—Tyrian Rose, Plate 24/1, sometimes with a streak of White, and with point of attachment Sulphur Yellow, Plate 1/2; inside surface—Iridescent Crimson, Plate 22, with point of attachment Aureolin, Plate 3/1.

This description was made from a rose that was open for three days outdoors in early September, at West Grove, Pennsylvania, U. S. A.:

*Color.*—Outer petal: outside surface—Spirea Red, Plate 025/1, shading to Rose Madder, Plate 23/1 towards base of petal, and with point of attachment Sulphur Yellow, Plate 1/2; inside surface—Rose Bengal, Plate 25/1, shading to Rose Bengal, Plate 25 towards base, with point of attachment Aureolin, Plate 3/1. Inner petal: outside surface—Spirea Red, Plate 025/1, shading to Crimson, Plate 22/1, with point of attachment Sulphur Yellow, Plate 1/2; inside surface—Rose Red, Plate 724/1, shading to Iridescent Rose Red, Plate 724, with point of attachment Aureolin, Plate 3/1.

*General color effect.*—Newly opened flower—Iridescent Spirea Red, Plate 025/1, shaded with Rose Bengal, Plate 25/1, and with inside of petals showing Rose Red, Plate 724; colors subject to change with climate; in cool, cloudy weather, the colors clear to a color range from Cardinal Red, Plate 822, to Blood Red, Plate 820/1. Three days open—Iridescent Spirea Red, Plate 025/1, showing some Rose Bengal, Plate 25, and Rose Red, Plate 724/1 at center; colors subject to change with climate; in cool, cloudy weather, the colors clear to a color range from Cardinal Red, Plate 822, to Blood Red, Plate 820/1.

*Behavior.*—Drop off cleanly; affected by cold weather by clearing of Spirea Red coloration to nearly Cardinal Red.

*Flower longevity.*—On bush in garden—4 days in October. Cut roses grown outdoors and kept at living-room temperatures—5 days in October.

*Reproductive organs*

Stamens: Medium number; arranged regularly about pistils; mixed with petaloids.

Filaments: Many; most with anthers; medium length. Color—Indian Orange, Plate 713/1.

Anthers: All open at once; medium size; occasionally an anther fused with a petaloid. Color—Mimosa Yellow, Plate 602.

Pollen: Abundant. Color—Lemon Yellow, Plate 4.

Pistils: Medium number.

Styles: Uneven; medium length; thin; bunched.

Stigma: Color—white.

Ovaries: All enclosed in receptacle.

Hips: None observed.

Sepals: Permanent; medium length; spear-shaped.

Seeds: None observed.

*Plant*

Foliage:

*Leaves.*—Compound of 5 leaflets; normal abundance; medium size; moderately leathery.

*Leaflets.*—Shape—from oval to ovoid, with apex acute. Base—Obtuse. Margin—simply serrate.

*Color.*—Mature: upper surface—Parsley Green, Plate 00962; under surface—Sage Green, Plate 000861/1. Young: upper surface—Oxblood Red, Plate 00823/1, overlying Parsley Green, Plate 00962/1; under surface—Indian Lake, Plate 826, overlying Willow Green, Plate 000862.

*Rachis (the supporting stem of the compound leaf).*—Medium caliper. Upper side—grooved; hairy. Under side—sparsely thorny.

*Stipules.*—Long; moderately narrow; with points of medium length turning out at an angle of 45°.

*Disease resistance.*—Comparable to average climber varieties growing under the same cultural conditions at West Grove, Pennsylvania, U. S. A.

Growth:

*Habit.*—Climbing; much-branched.

*Growth.*—From free to vigorous.

*Canes.*—Medium heavy.

*Main stems.*—Color—green. Thorns—several; medium length; hooked downward; with oval base of medium length. Prickles—several; color—bronze. Hairs—none.

*Branches.* — Color — Lettuce Green, Plate 861. Thorns—several; medium length; hooked downward; with oval base of medium length. Prickles—several; color—bronze. Hairs—none.

*New shoots.*—Color—Lettuce Green, Plate 861, overlaid with Garnet Brown, Plate 00918/1. Thorns—several; medium length; hooked downward; with oval base of medium length. Prickles—none. Hairs—none.

I claim:

A new and distinct variety of rose plant of the large-flowered climber class, substantially as herein shown and described, characterized particularly as to novelty by its vigorous habit of growth, its good hardiness, its abundant and attractive foliage, its very good remontance, its habit of producing a terminal bloom on each new shoot, the very good form and size of its blooms, the strong and appealing fragrance of its blooms, and the iridescent Spirea Red general color tonality of its blooms which clears to Iridescent Cardinal Red in cool weather.

No references cited.